(12) United States Patent
Lim et al.

(10) Patent No.: US 11,185,424 B2
(45) Date of Patent: Nov. 30, 2021

(54) ALIGNMENT GUIDE FOR ACETABULAR IMPLANT SURGERY AND METHODS FOR USE

(71) Applicant: Advanced Ortho-Med Technology, Inc., Castro Valley, CA (US)

(72) Inventors: Sok Gek Lim, Castro Valley, CA (US); GuanMing Zhou, Foshan (CN)

(73) Assignee: Advanced Ortho-Med Technology, Inc., Castro Valley, CA (US)

( * ) Notice: Subject to any disclaimer, the term of this patent is extended or adjusted under 35 U.S.C. 154(b) by 87 days.

(21) Appl. No.: 16/349,130

(22) PCT Filed: Nov. 8, 2017

(86) PCT No.: PCT/US2017/060698
§ 371 (c)(1),
(2) Date: May 10, 2019

(87) PCT Pub. No.: WO2018/093640
PCT Pub. Date: May 24, 2018

(65) Prior Publication Data
US 2019/0269525 A1 Sep. 5, 2019

Related U.S. Application Data

(60) Provisional application No. 62/422,239, filed on Nov. 15, 2016.

(51) Int. Cl.
*A61F 2/46* (2006.01)
*A61B 17/17* (2006.01)
*A61B 34/10* (2016.01)

(52) U.S. Cl.
CPC ........ *A61F 2/4609* (2013.01); *A61B 17/1746* (2013.01); *A61B 2034/102* (2016.02); *A61B 2034/105* (2016.02); *A61B 2034/108* (2016.02); *A61F 2002/4687* (2013.01)

(58) Field of Classification Search
CPC ............... A61F 2/4609; A61B 17/1746; A61B 2034/108
See application file for complete search history.

(56) References Cited

U.S. PATENT DOCUMENTS 6,395,005 B1 * 5/2002 Lovell .................... A61F 2/4657
606/91
2016/0287408 A1 * 10/2016 Witt .......................... A61F 2/34

* cited by examiner

*Primary Examiner* — Christian A Sevilla
(74) *Attorney, Agent, or Firm* — Ballard Spahr LLP

(57) ABSTRACT

An alignment guide for acetabular implants is designed to fit a particular patient using 3D medical imagery, conforms to the patient and uses one or more guide holes to direct the insertion of a positioning pin to indicate the correct positioning of various surgical tools during a medical procedure.

9 Claims, 4 Drawing Sheets

ALIGNMENT GUIDE FOR ACETABULAR IMPLANT SURGERY AND METHODS FOR USE

CROSS REFERENCE TO RELATED APPLICATIONS

This application claims priority to U.S. Provisional Patent Application No. 62/422,239, filed on Nov. 15, 2016 in the United States Patent and Trademark Office (USPTO).

INTRODUCTION

The present teachings provide a method for the construction of personalized patient and instrument systems for the precision positioning of acetabular implants. Surgeons have previously relied solely on their own judgement and skill in placing the implants and existing surgical guide systems are disfavored by doctors as they require long setup times and are costly to buy and maintain.

Therefore, there is need for a new system of precision positioning surgical instruments during acetabular implant procedures that is personalized to fit the patient, and that is quick and easy to setup and adjust. The following presents an invention intended to satisfy these needs.

BRIEF SUMMARY OF THE INVENTION

The present invention provides a personalized design and 3D printing surgical guide for positioning an acetabular implant. The present teachings provide a method for the construction of personalized device for the precision positioning of acetabular implants. The method includes devising a personalized pre-surgical plan from the patient radiographic images, including, but not limited to X-rays, CT and MR images and choice of commercially available surgical instruments from a range of manufacturers for use in the surgery.

The process for the personalized pre-surgical plan comprises the following steps: a 3D modelling module that constructs a 3D model of the patient acetabulum from the radiographic images; a quantification module for obtaining the required measurements from the 3D model including, in order to find the best fit acetabular cup size and pre-surgical plan for reaming and inserting the acetabular implant; a designing module of the personalized devices from the 3D model of the patient and specifications of the surgical instruments; and a manufacturing module to produce the personalized devices, including, but not limited to, 3D printing technology of these personalized devices and sterilized for use during the surgery. The personalized device is patient-personalized, easy to use, independent of patient positioning on the surgical table and the surgical table positioning.

According to various embodiments, an alignment guide comprises a head constructed from a 3D model that is reconstructed from CT, MR or similar images of a patient and that is conformed to and engages part of the patient's pelvis, an extension attached to the head that contains one or more guide holes, and one or more positioning pins that can be inserted through the guide holes into the patients pelvis and then indicate the correct direction and angle for the insertion of the acetabular cup and associated instruments, including, but not limited, to reamers, impactors and acetabular cup implant tools.

According to various embodiments, the part of the pelvis to which the head is conformed can be the patient's acetabulum.

According to various embodiments, the extension can possess a handle.

According to various embodiments, the handle can possess one or more additional guide holes.

According to various embodiments, the extension can rotate while the head is secure in the patient's pelvis.

According to various embodiments, the head can possess one or more claws to secure it to the pelvis of the patient.

According to various embodiments, the positioning pin can possess a clamp which can hold surgical instruments and be attached after the positioning pin has been inserted into the patient's pelvis.

According to various embodiments, the alignment guide can also have a means for controlling the depth of surgical instruments.

According to various embodiments, the means for controlling the depth of surgical instruments can be a physical block that attaches to surgical instruments.

According to various embodiments, a method for using an alignment guide comprises providing the alignment guide, aligning the head into the part of the patient for which it has been shaped, inserting one or more positioning pins into said patient's pelvis through the guide holes, attaching a clamp to a positioning pin, and using the positioning pin or clamp to guide surgical instruments during a procedure.

BRIEF DESCRIPTION OF FIGURES

The present teachings will become more fully understood from the detailed description and the accompanying drawings, wherein.

DETAILED DESCRIPTION OF THE INVENTION

In the Summary of the Invention above and in the Detailed Description of the Invention, and in the claims below, and in the accompanying drawings, reference is made to particular features (including method steps) of the invention. It is to be understood that the disclosure of the invention in this specification includes all possible combinations of such particular features. For example, where a particular feature is disclosed in the context of a particular aspect or embodiment of the invention, or a particular claim, that feature can also be used, to the extent possible, in combination with and/or in the context of other particular aspects and embodiments of the invention, and in the invention generally.

The term "comprises" and its grammatical equivalents thereof are used herein to mean that other components, ingredients, steps, etc. are optionally present. For example, an article "comprising" (or "which comprises") components A, B, and C can consist of (i.e. contain only) A, B, and C, or can contain not only components A, B, and C but also one or more other components.

When reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having "an upper limit or no upper limit, depending of the variable being defined). For example, "at least 1" means 1 or more than 1. The term "at most" followed by a number is used herein to denote the end of a range ending with that number (which may be a range having 1 or 0 as it's lower limit, or a range having no lower limit, depending on the variable being defined). For example, "at most 4" means 4 or less than 4, and "at most 40%" means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm.

Definitions

"CT" IS COMPUTERIZED TOMOGRAPHY AND GRAMMATICAL EQUIVALENTS;
"MR" IS MAGNETIC RESONANCE AND GRAMMATICAL EQUIVALENTS;

The following description is exemplary in nature and is not intended to limit the present teachings, applications and uses in any way.

Figure 1:
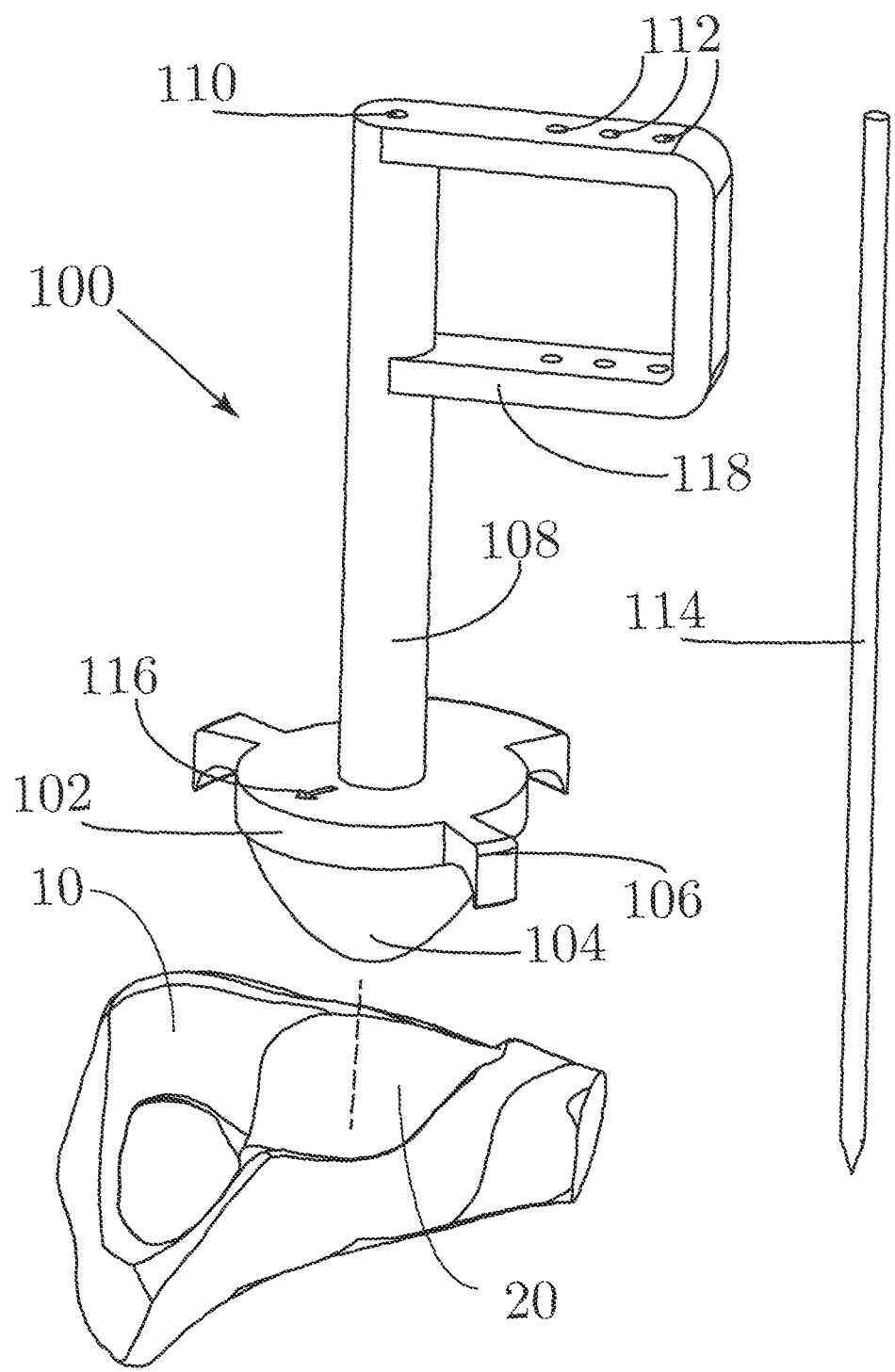
FIG. 1 is a perspective, exploded view of the alignment guide and its relation to a patient's pelvis.

The teachings provide a method that includes devising a personalized pre-surgical plan to design and produce a personalized device for precision positioning of acetabular implants. FIG. 1 shows an exemplary alignment guide for acetabular implant surgery 100 according to the present invention. It features two detachable components, the head 102 and the extension 108. The alignment guide 100 is designed from the patient radiographic images and the choice of the surgical instruments to be used in the surgery, including, but not limited to reamers, impactors and acetabular cup insertion devices; and manufactured using 3D printing technology or any other suitable manufacturing process.

The process for the pre-surgical plan comprises the following steps: a 3D modeling module that constructs a 3D model of the patient acetabulum from the radiographic images, including, but not limited to X-rays, CT and MR images; a quantification module for obtaining the required measurements from the 3D model including, but not limited to, the diameter of the acetabulum and the centroid of the acetabulum, and the anteversion and abduction angles, in order to find the best fit acetabular cup size and precision positioning for reaming and inserting the acetabular implant; a designing module of the personalized devices from the 3D model of the patient and specifications of the surgical instruments, the design of the personalized devices is based on quantitative measurements such as the anteversion and abduction angles, and the dimensions of the chosen surgical instruments to ensure that the surgery conforms to the pre-surgical plan. Suitable and related acetabular landmarks are also used for the design of the personalized device and a manufacturing module is used to produce the personalized devices, including, but not limited to 3D printing technology. The personalized device is then sterilized for use during the surgery. The personalized device is easy to use and independent of patient positioning on the surgical table and the surgical table positioning.

FIG. 1 shows an exemplary alignment guide possessing numerous advantageous features. The head 102 is designed through the above pre-surgical process and its lower portion 104 is designed to fit exactly into a portion of the surgical patient's pelvis 10. FIG. 1 shows a head 102 that has been designed to exactly fit the patient's acetabulum 20. The head 102 may also feature claws 106 that grip onto portions of the patient's pelvis 10, further securing the alignment guide 100 for inserting of the positioning pins 114. The head may also feature an indicator 116 that indicates the proper direction and alignment of implants during surgery.

Attached to the head 102 is the extension 108. The extension possesses one or more guide holes 112 through which positioning pins 114 can be inserted and aligned for entry into the pelvis 10 of the surgical patient. The head 102 can be attached to the extension 108 by a rotating axle 110 that connects the head 102 and extension 108. The rotating axle 110 allows the user of the alignment guide 100 to move the guide holes 112 to many different positions during a surgical procedure.

The extension 108 may possess a handle 118 which is designed and added at an angle determined by the anteversion and abduction angles. The handle 118 may also possess one or more guide holes 112. When the alignment guide 100 is inserted into the portion of the patient's pelvis 10 it has been customized for (in FIG. 1 the patient's acetabulum 20), the handle is thus at an angle which allows for the easy alignment and insertion of positioning pins 114.

The head 102 can be formed of any 3D printable material suitable for sterilization and use for surgery such as, but not limited to, nylon polymer. The rest of the alignment guide 100 can be made of any material suitable for sterilization and use for surgery such as, but not limited to, surgical stainless steel.

Figure 2:
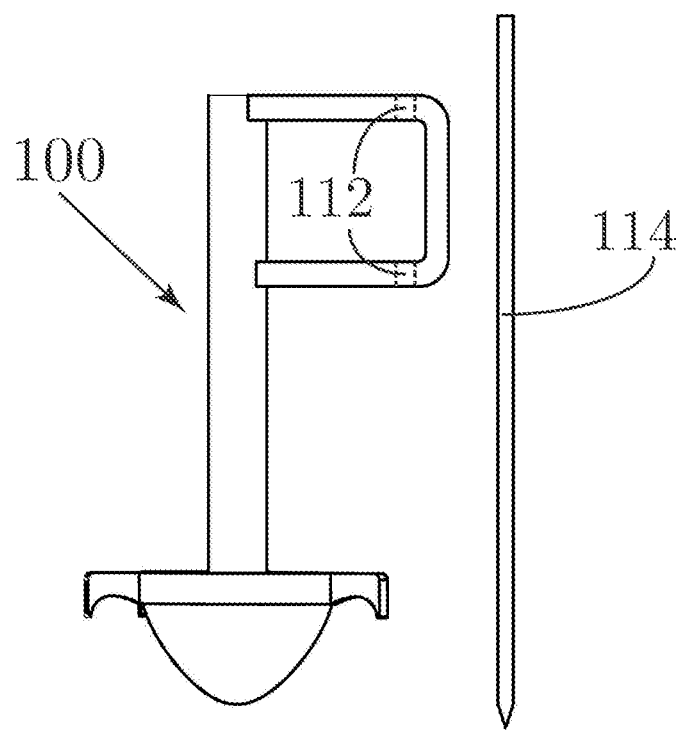
FIG. 2 is a side view of an exemplary alignment guide indicating exemplary positions of guide holes.
Figure 3:
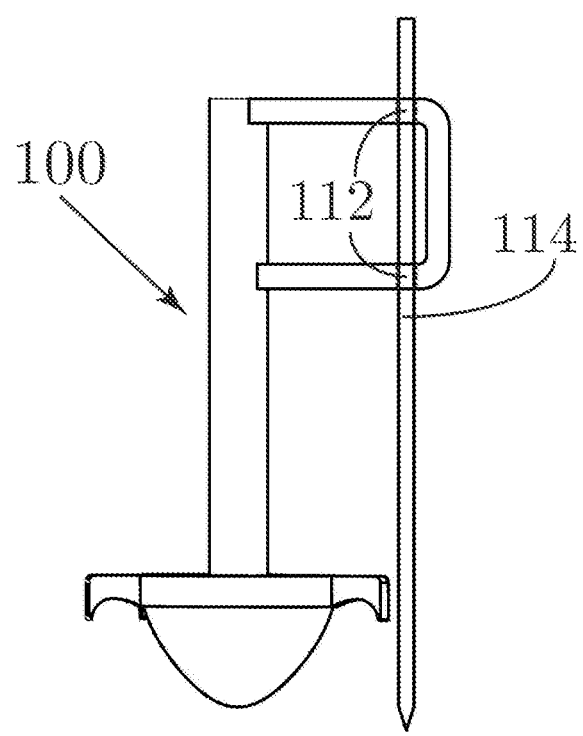
FIG. 3 is side view of an exemplary alignment guide where the positioning pin has been inserted through the guide holes.

FIGS. 2 and 3 show side views of the alignment guide 100 and exemplary positions for guide holes 112. FIG. 3 shows a positioning pin 114 that has been inserted through the guide holes and is now aligned and ready for insertion into the patient's pelvis. Once the positioning pin 114 is inserted into the patient's pelvis 10 the rest of the alignment guide can be removed.

Figure 4:
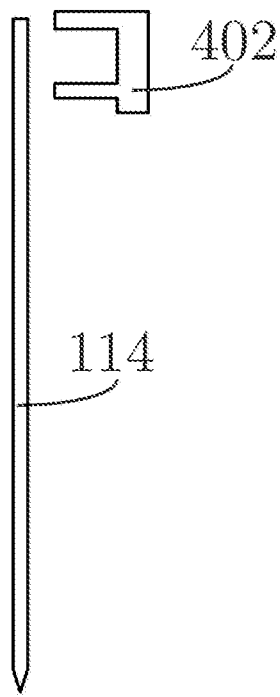
FIG. 4 is a side view of an exemplary positioning pin and clamp.
Figure 5:
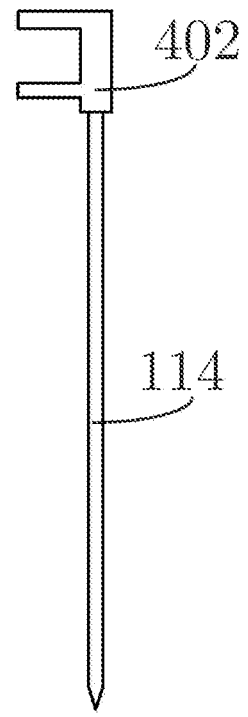
FIG. 5 is a side view of an exemplary positioning pin and clamp wherein the clamp has been secured to the top of the positioning pin.

FIGS. 4 and 5 show side views of an exemplary positioning pin 114 and clamp 402. FIG. 5 shows the clamp 402 after being secured to a positioning pin 114.

The clamp 402 can be designed to fit and stabilize a plurality of commercially available reamers with different cross-sectional shape and sizes or other surgical tools used during acetabular procedures such as but not limited to, impactors and acetabular cup inserters with different cross-sectional shapes and sizes.

The positioning pin 114 can be made of any material suitable for sterilization and use for surgery such as, but not limited to, surgical stainless steel.

The clamp 402 can be made of any 3D printable material suitable for sterilization and use during surgery including nylon polymer, but can also be made from other materials suitable for use during surgery such as, but not limited to, surgical stainless steel.

Figure 6:
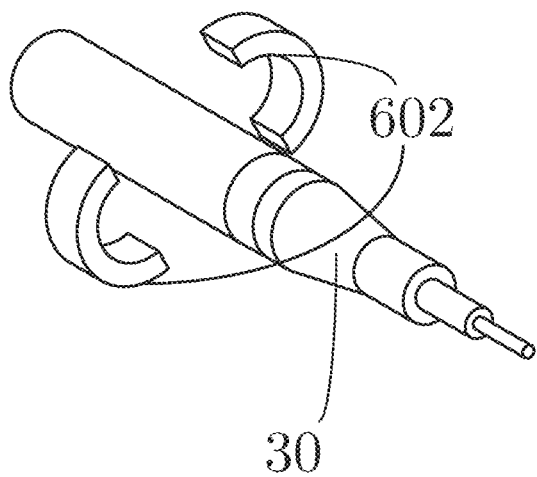
FIG. 6 is a perspective view from above of an exemplary depth controller of a version of the present invention.
Figure 7:
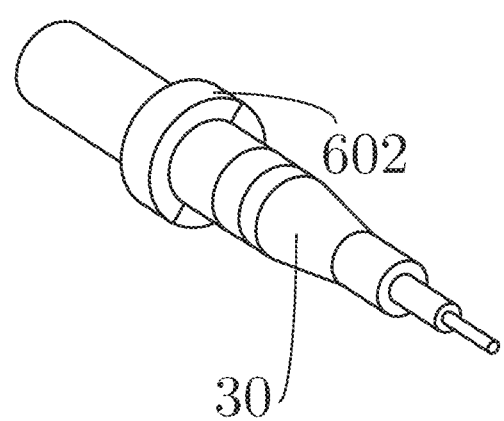
FIG. 7 is a perspective view from above of an exemplary depth controller, after having been applied to a surgical tool.

As shown in FIG. 6, the system can also feature a depth controller 602 to prevent over/under reaming of the acetabulum 20. The depth controller 602 can be a ring structure that attaches to a surgical instrument 30 by physically blocking the surgical tool from moving through the clamp 402 beyond a desired depth. It can also be a visual indicator applied to the surgical tool, giving the user a visual mark for when to stop lowering the surgical instrument 30.

The surgical instruments to be used during the surgery are chosen by the surgeon during the development of the pre-surgical plan. The surgeon may choose to employ instruments from a plurality of manufacturers with different cross-sectional shapes and sizes. Depending on the choice of instruments, it may be necessary to design more than one clamp 402 to fit the dimensions of the various instruments. This allows the surgical team performing the procedure to select whatever tools they feel will be the best for that particular procedure without having to consider the relative compatibility of various tools and manufacturers.

Although the present invention has been described in considerable detail with reference to certain preferred versions thereof, other versions are possible. Therefore, the spirit and scope of the appended claims should not be limited to the description of the preferred versions contained herein.

We claim:

1. A patient-specific alignment guide, comprising:
   a head;
   an extension;
   one or more positioning pins;
   said head being constructed from a 3D model that is reconstructed from CT, MR or similar images of a patient and that is conformed to and engages part of said patient's pelvis;
   said extension being attached to said head and possessing one or more guide holes through which a positioning pin can be inserted into said patient's pelvis; and
   wherein said extension is attached to said head by a rotating axle, such that said extension may pivot while said head is secured in said patient's pelvis.

2. The patient-specific alignment guide of claim 1 wherein, said part of the pelvis is said patient's acetabulum.

3. The patient-specific alignment guide of claim 1 wherein, said extension possesses a handle.

4. The patient-specific alignment guide of claim 3 wherein, said handle possesses one or more additional guide holes.

5. The patient-specific alignment guide of claim 1 wherein, said head of said patient-specific alignment guide possesses one or more claws to secure it to said patient's pelvis.

6. The patient-specific alignment guide of claim 1 wherein, said positioning pin possesses a clamp which can be placed on said positioning pin after it has been inserted into said patient;
   said clamp formed such that it can hold or guide surgical tools.

7. The patient-specific alignment guide of claim 6 further comprising a depth controller for controlling the depth of surgical instruments.

8. The patient-specific alignment guide of claim 7 wherein said depth controller is a ring structure that attaches to said surgical instruments.

9. A method for using the device of claim 1 comprising the following steps:
   a. providing a patient-specific alignment guide of claim 1;
   b. aligning said head into said part of the patient's pelvis for which it has been shaped;
   c. inserting one or more said positioning pins into said patient's pelvis, using one or more said guide holes;
   d. attaching a clamp to one of said positioning pins;
   e. using said positioning pins and said clamp to guide one or more surgical instruments including, but not limited to, reamers, impactors and acetabular cup implant tools during a surgical procedure.

* * * * *